United States Patent
Antenbring et al.

(10) Patent No.: US 6,655,384 B2
(45) Date of Patent: Dec. 2, 2003

(54) METHOD OF RETAINING A GASTRIC TUBE

(76) Inventors: Colin Antenbring, #3 -2035 West 4th Avenue, Vancouver British Columbia (CA), V6J 1N3; Ron Gorospe, #801 - 5750 Larch Street, Vancouver British Columbia (CA), V6M 4E2

( * ) Notice: Subject to any disclaimer, the term of this patent is extended or adjusted under 35 U.S.C. 154(b) by 0 days.

(21) Appl. No.: 10/022,694

(22) Filed: Dec. 20, 2001

(65) Prior Publication Data

US 2003/0116161 A1 Jun. 26, 2003

(51) Int. Cl.[7] .............................................. A61M 16/00
(52) U.S. Cl. .......................... 128/207.14; 128/200.26; 128/DIG. 26; 128/912
(58) Field of Search ........................ 128/207.14, 207.15, 128/207.17, 207.18, DIG. 26, 200.26, 912

(56) References Cited

U.S. PATENT DOCUMENTS

| | | | | |
|---|---|---|---|---|
| 3,730,179 A | * | 5/1973 | Williams | 128/204.18 |
| 4,090,518 A | * | 5/1978 | Elam | 128/207.15 |
| 4,446,864 A | * | 5/1984 | Watson et al. | 128/207.14 |
| 4,848,331 A | * | 7/1989 | Northway-Meyer | 128/200.26 |
| 5,009,227 A | * | 4/1991 | Nieuwstad | 128/207.17 |
| 5,224,935 A | * | 7/1993 | Hollands | 604/180 |
| 5,368,024 A | * | 11/1994 | Jones | 128/207.17 |
| 5,437,273 A | * | 8/1995 | Bates et al. | 128/207.17 |
| 5,507,284 A | * | 4/1996 | Daneshvar | 128/207.14 |
| 5,868,132 A | * | 2/1999 | Winthrop et al. | 128/207.14 |

* cited by examiner

Primary Examiner—Aaron J. Lewis
Assistant Examiner—Mital Patel

(57) ABSTRACT

A method of intubating a patient includes inserting a tracheal tube into the patient, inserting a gastric tube into the patient, attaching a gastric tube retainer to the tracheal tube, and engaging the gastric tube in the gastric tube retainer to thereby secure the gastric tube in position relative to the tracheal tube. The gastric tube is engaged in the gastric tube retainer by spreading apart portions of the gastric tube retainer along a slit, and sliding the gastric tube into the gastric tube retainer along the slit to a gastric tube opening having a diameter corresponding to the outer diameter of the gastric tube, so that the gastric tube is securely retained in an uncompressed condition in the gastric tube opening.

5 Claims, 6 Drawing Sheets

US 6,655,384 B2

METHOD OF RETAINING A GASTRIC TUBE

BACKGROUND OF THE INVENTION

1. Field of the Invention

The present invention relates to methods of retaining gastric tubes and more particularly to methods of securing a gastric tube relative to an intubated patient.

2. Description of the Related Art

A gastric tube, commonly called a Salem tube, is a hollow plastic tube usually made of polyvinylchloride (PVC), that is inserted through the nose or mouth, down the back of the throat, through the esophagus and into the stomach. Gastric tubes are commonly used in the treatment of patients in order to provide nutrition and/or for stomach emptying. Generally, gastric tubes inserted into the stomach are made stiff to resist collapsing when suction is applied. Gastric emptying is effected to prevent vomiting or to monitor how well a patient is tolerating being fed into the stomach. If the patient is not tolerating being fed into the stomach, the patient may tolerate being fed into the duodenum (past the stomach) via a longer duodenal tube. This duodenal feeding tube is made smaller, thinner and softer than a gastric tube because it is used just for feeding and not for stomach emptying. The duodenal feeding tube is weighted on its end and has a guide wire to aid the clinician in inserting this tube into the duodenum.

Gastric tubes are available in six common sizes: 8, 10, 12, 14, 16, and 18 French (roughly 0.08 to 0.24 inches in outer diameter). The choice in size to use for a patient may relate to the size of the patient or the primary purpose of the gastric tube. Generally, for unconscious patients, bigger tubes are easier to insert, as they are more rigid and therefore resist curling in the oropharynx. Larger tubes also have less resistance and promote better flow and have less chance of obstructing.

The securing of gastric tubes to critically ill patients has been a problem for many years. Past and current devices used to secure gastric tubes usually comprise an adhesive material. Tape is widely used because it is inexpensive and readily available. Different types of tape can be used and it is usually wrapped around the gastric tube and then stuck to the patient's nose or face.

However, tape may come loose or may cause pressure sores by holding the gastric tube too tightly to the nostril and the patient can pull his/her gastric tube out fairly easily if it is only taped in place. Tape provides an inconsistent hold, depending on the type of tape used and the technique for applying it. Also, the presence of moisture and/or oil from the patient's skin can cause tape to loosen with time. As a backup, some hospitals tape the gastric tube directly to the tracheal tube, if the patient is intubated, or use a safety pin with tape to secure the gastric tube to the patient's gown, providing additional security.

When using gloves, tape is difficult to handle, requiring the clinician to expose his or her hands to potentially infectious body fluids. Overall, tape is difficult to work with, takes longer to apply, and gives the patient an alarming appearance. Also, allergic reactions, skin irritations and nasal tissue necrosis have been reported from the use of tape. Replacing gastric tubes, and especially duodenal feeding tubes, is time consuming and costly, making it important to use a secure and reliable device.

If the gastric tube is taped to the tracheal tube, however, reference marks along the tracheal tube are obscured and repositioning is difficult.

Some tracheal tubes are accidentally cut too short prior to insertion, so that the hub of the tracheal tube is almost level with the patient's face. In this case, the gastric tube is usually just taped to the face of the patient.

BRIEF SUMMARY OF THE INVENTION

According to the present invention, a method of retaining a gastric tube, before or after insertion of a tracheal tube into a patient, comprises the steps of attaching a gastric tube retainer to an end portion of the tracheal tube and connecting the end portion of the tracheal tube to a ventilating circuit so as to secure the gastric tube retainer on the end portion of the tracheal tube, inserting the gastric tube into the patient, and engaging the gastric tube in the gastric tube retainer to thereby secure the gastric tube in position relative to the tracheal tube.

Preferably, the gastric tube retainer is made of sheet material and the gastric tube is engaged in the gastric tube retainer, before or after the attachment of the gastric tube retainer to the tracheal tube, by spreading apart portions of the gastric tube retainer along a slit, and sliding the gastric tube into the gastric tube retainer along the slit to a gastric tube opening having a diameter no greater than the outer diameter of the gastric tube, so that the gastric tube is retained in an uncompressed condition in the gastric tube opening in the gastric tube retainer.

BRIEF DESCRIPTION OF THE DRAWINGS

The invention will be more readily understood from the following description thereof, when taken in conjunction with the accompanying drawings, in which.

DESCRIPTION OF THE PREFERRED EMBODIMENTS

Figure 1:
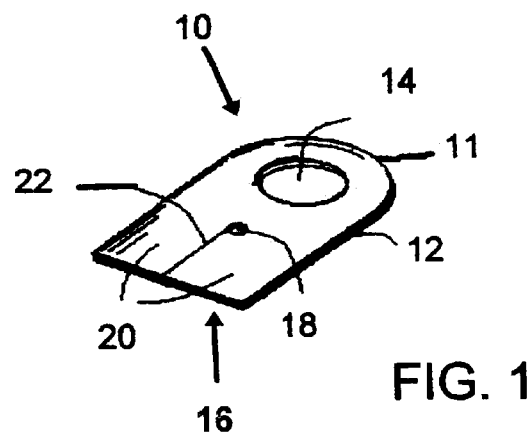
FIG. 1 is a perspective view of a gastric tube retainer embodying the present invention.
Figures 2, 3:
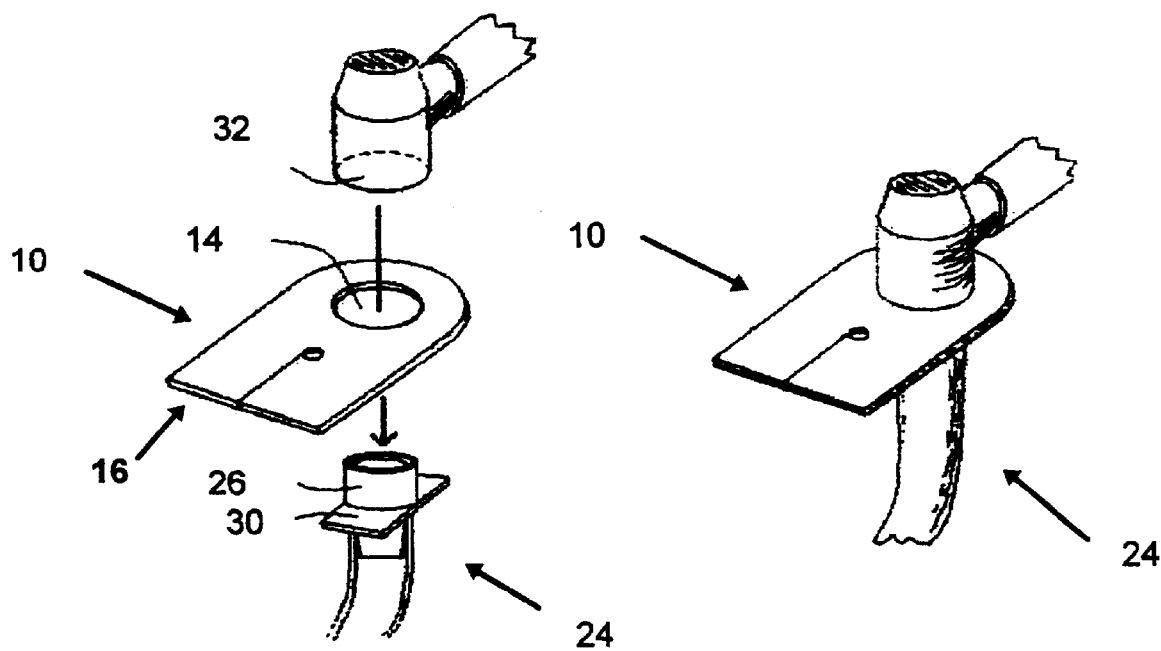
FIG. 2 is an exploded perspective view illustrating a step in the assembly of the retainer of FIG. 1 with a tracheal tube.
FIG. 3 shows a view in perspective of a completed assembly of the retainer and the tracheal tube of FIG. 2.

FIGS. 1 and 2 show a gastric tube retainer, indicated generally by reference numeral 10, which comprises a flat sheet or strip-shaped plastic material piece or lamina. One end 11 of the retainer 10 is rounded at the periphery of the retainer 10, for safety, and has a tracheal tube opening 14. An opposite end forms a gastric tube engagement portion indicated generally by reference numeral 16, which includes a gastric tube opening 18, and a pair of flaps 20 separated by a slit 22 extending from the gastric tube opening 18 to the periphery of the retainer 10.

To assemble the retainer 10 on a tracheal tube indicated generally by reference numeral 24, a hub 26 on the tube is then inserted through the tracheal tube opening 14 in frictional engagement with the retainer 10, which then abuts a flange 30 of the tracheal tube 24. An elbow or swivel adapter 32, forming a component of a ventilating circuit, as will be readily apparent to those skilled in the art, is then connected to the hub 26, as shown in FIG. 3.

Figure 4:
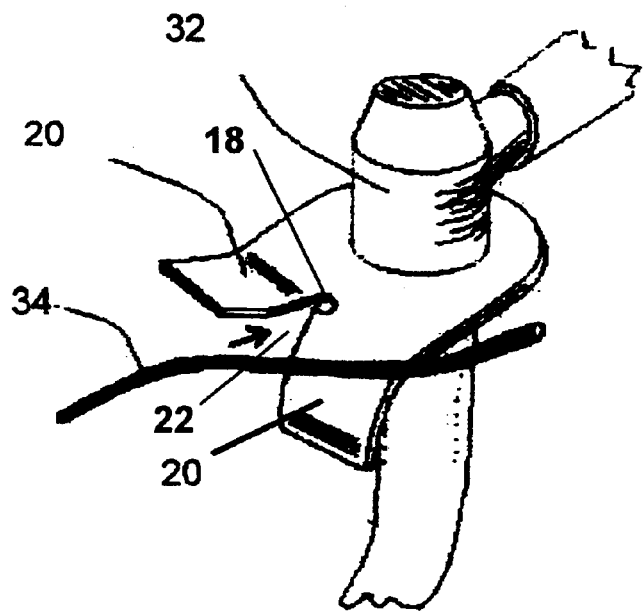
FIG. 4 shows a view similar to that of FIG. 3 but with the retainer being flexed to allow a gastric tube to be engaged with the retainer.
Figure 5:
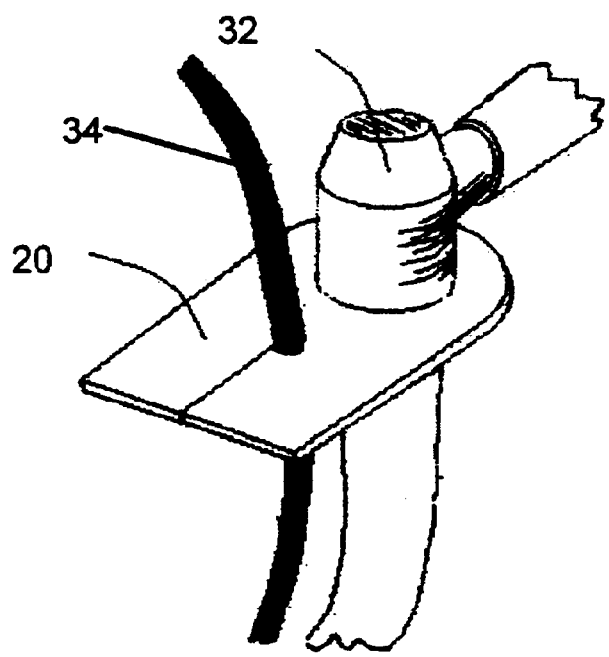
FIG. 5 shows a view similar to that of FIG. 4 but with the gastric tube engaged and held by the retainer.

Then, as shown in FIG. 4, the engagement portion 16, which is resiliently flexible, is flexed to separate the flaps 20 and open the slit 22 and thereby to permit a gastric tube 34 to be inserted through the slit 22 into the gastric tube opening 18. The flaps 20, when released, return resiliently to their original positions, so that the gastric tube engagement portion 16 is thereby releasably engaged around the gastric tube 34.

The retainer 10 is thin enough so as not to impede the fit between the elbow connector/swivel adapter 32 and the hub 26 of the tracheal tube 24.

Alternatively, the gastric tube retainer 10 can be engaged, in the manner described above, with the gastric tube 34 before being attached to the tracheal tube 24.

Figure 6:
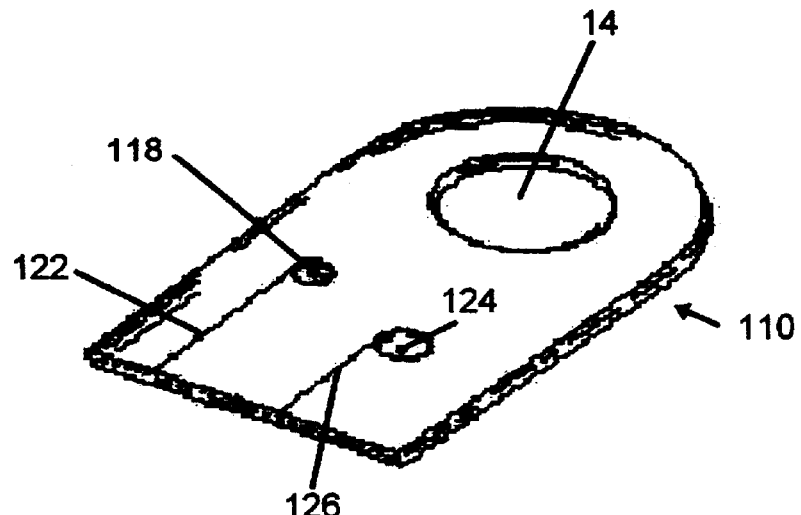
FIG. 6 shows a modification of the retainer of FIG. 1 for use with gastric tubes of two different sizes.

FIG. 6 shows a modification of the retainer 10, indicated generally by reference numeral 110, which has a gastric tube opening 118 and a slit 122 corresponding to the opening 18 and the slit 22 of FIG. 1 and a further gastric tube opening 124, which has a larger diameter than the opening 118 so as to fit a correspondingly larger gastric tube outer diameter, and a further slit 126 extending from the opening 124. The slits 122 and 124 in FIG. 6 are spaced far enough apart so as not to impede the resilient memory of the retainer 110. The slits 122 and 124 differ in length so that the openings 118 and 124 can be spaced apart sufficiently without having to make the retainer 110 wider.

Figure 7:
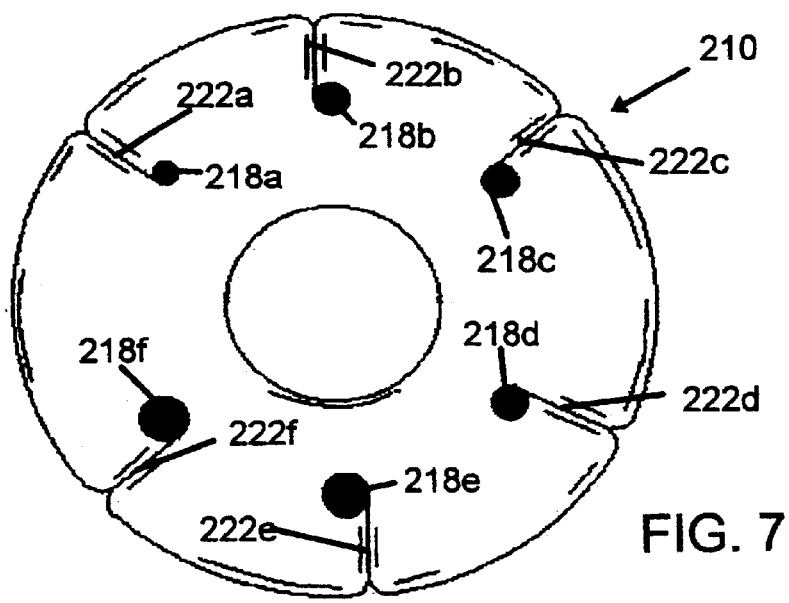
FIG. 7 shows a plan view of a further modification of the retainer of FIG. 1.
Figure 8:
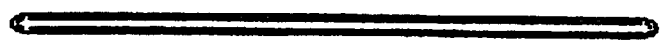
FIG. 8 shows a view in side elevation of the retainer of FIG. 7.

The modified retainer of FIGS. 7 and 8, which is indicated generally by reference numeral 210, comprises a flat and circular disc-shaped retainer formed with six gastric tube openings 218a–f of different sizes, for receiving six correspondingly differently sized gastric tubes (not shown). Each of the openings 218a–f has a respective slit 222a–f extending from it to the periphery of the retainer 210, the openings 218a–f and the slits 222a–f being distributed around a central tracheal tube opening 214 so that the gastric tube engagement portion is an annular portion of the retainer 210 extending around the opening 214.

In use, one of the above-described retainers is pushed onto the tracheal tube hub 26 before or after a patient has been intubated. The swivel or elbow adapter 32 of the ventilating circuit is connected to the hub so the patient can be ventilated. As soon as the patient has thus been intubated, the patient is immediately ventilated either manually or mechanically. The gastric tube is then inserted into the patient via the mouth or nose and the adapter 32 is disconnected from the hub 26 to allow the latter to be inserted into the tracheal tube opening of the retainer 10, 110 or 210.

Figure 9:
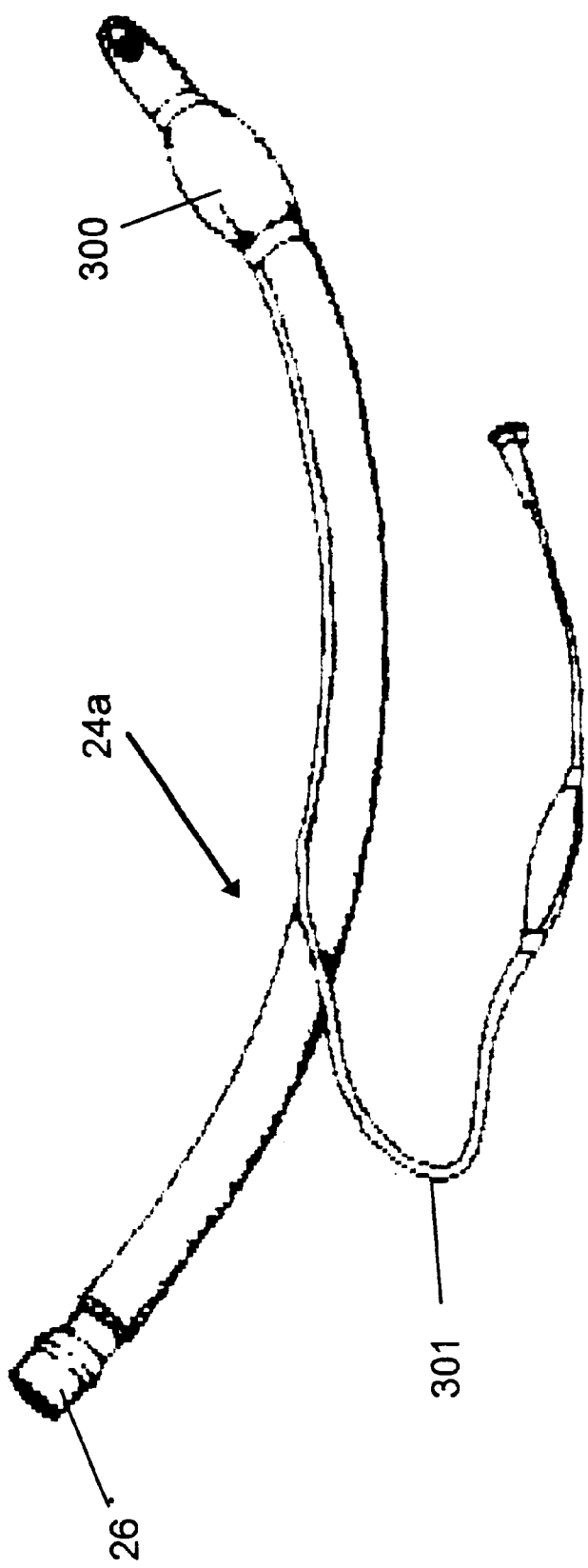
FIG. 9 shows a view in side elevation of a tracheal tube.

FIG. 9 of the accompanying drawings illustrates a part of the conventional tracheal tube, which is indicated generally by reference numeral 24a and which is provided, at it's the distal end, with a cuff 300. As will be apparent to those skilled in the art, the cuff 300 is expanded, by being inflated, to the wall of the tracheal passage of a patient when the tracheal tube is in use. For that purpose, the tracheal tube 24 is provided with an auxiliary tube 301 through which air can be passed into the cuff 300. The hub 26 is provided that the proximal end of the tracheal tube 24.

Figure 10:
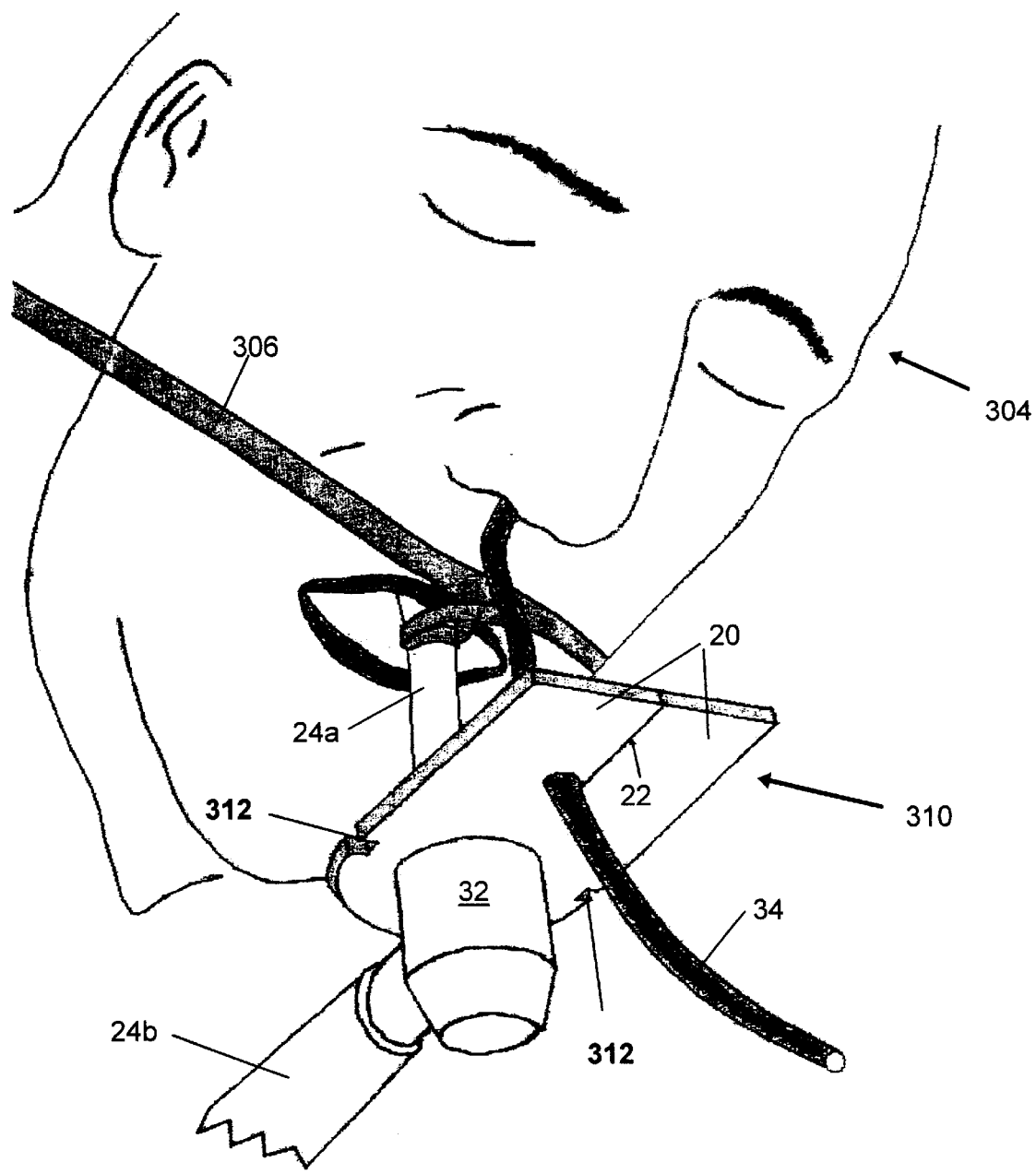
FIG. 10 shows a view in perspective of a modification of the gastric tube retainer of FIG. 1 being installed in an intubated patient.

Referring now to FIG. 10 of the accompanying drawings, the method of intubation of a patient, employing a gastric tube retainer 310, which is a modification of the gastric tube retainer 10, will now be described. Parts of the gastric tube retainer 310 which are similar to corresponding parts of the gastric tube retainer 10 have been identified by the same reference numerals and, for convenience, will not be described again herein.

Figure 11:
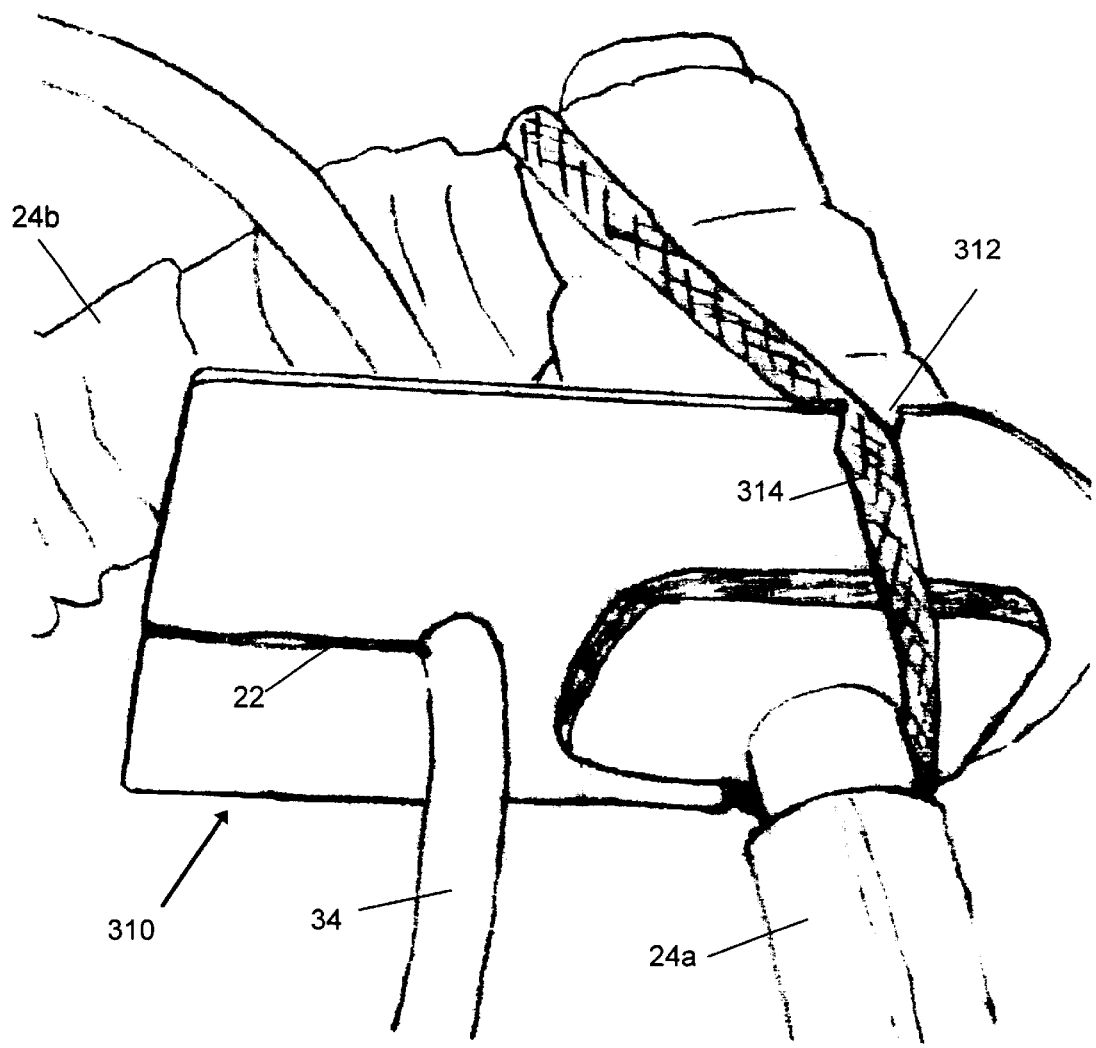
FIG. 11 shows a view in perspective of the room modified gastric tube retainer of FIG. 10 secured by an elastic band.

The gastric tube retainer 310 differs from the gastric tube retainer 10 by having notches or cutouts 312 formed in its opposite side edges, as shown in FIGS. 10 and 11.

As shown in FIG. 10, the tracheal tube 24 has been inserted into the mouth of a patient whose head is indicated generally by reference numeral 304. The tracheal tube 24 is secured in position on the patients head 304 by means of a tape 306 or a cotton twill tie or other tie, which is wrapped around the patient's face and the back of his neck. The end of the tracheal tube 24 protruding from the patient's face is then inserted through the tracheal tube opening 14 in the retainer 310, after which the elbow 32 is reconnected with the hub 26.

The flaps 20 of the gastric tube retainer 310 are then spread apart to enable the gastric tube 34 to be slid into the gastric tube retainer 310 along the slit between the flaps 20 to the gastric tube opening 18. Then, an elastic band 314 is engaged in the notches 312 and around the tracheal tube 24, as shown in FIG. 11, to secure the gastric tube retainer 310 in position relative to the tracheal tube 24.

In each case, the tracheal tube acts as an anchor once the gastric tube is engaged into the retainer and by situating the retainer on the tracheal tube, some complications associated with tape can be avoided. There is no added discomfort or significant weight to the tracheal tube from the retainer and the retainer is metal and latex-free, making it safe for X-rays and MRI. The retainer allows quick positional adjustments of the gastric tube, thus saving valuable time. Moreover, the retainer will help prevent the costs and discomfort associated with the re-insertion of gastric tubes in intubated patients. The present invention avoids the use of unreliable adhesive materials for attachment, and can provide a consistent securement for an extended period of time. Unlike most other holding means, the present retainer does not have to touch the patient, thus avoiding possible discomfort to the patient.

The present retainer is particularly suitable for holding a gastric tube inserted through the mouth since, in that case, the gastric tube cannot be taped to the patient's nose. When the retainer is in use and the gastric tube is pulled, the retainer is designed to flex and hold instead of letting the gastric tube slide through. The present retainers will secure gastric tubes fast, provide quick repositioning and will last longer than tape.

In each of the gastric tube openings of the gastric tube retainers of the present invention, the diameter of the gastric tube opening is selected, corresponding to the outer diameter of a corresponding standard gastric tube, so that the gastric tube is engaged around its entire outer surface by the thin retainer to enhance the area of contact of the retainer with the tube in order to keep the gastric tube from being displaced from the patient, while not gripping the gastric tube so tightly that the luminal diameter of the gastric tube becomes constricted. The gastric tube opening diameter is thus selected to ensure that the retainer does not pierce, kink or pinch the outer surface of the gastric tube and also to ensure that the gastric tube is held securely in position by the gastric tube retainer.

We claim:

1. A method of retaining a gastric tube, comprising the steps of:

inserting an end portion of a tracheal tube through a tracheal tube opening in a gastric tube retainer;

connecting an end portion of a ventilating circuit to said end portion of said tracheal tube so as to secure gastric tube retainer between said end portions; and releasably engaging said gastric tube in a gastric tube opening in said gastric tube retainer to retain said gastric tube to said tracheal tube.

2. A method of retaining a gastric tube relative to a patient after insertion of a tracheal tube into the patient, comprising the steps of:

inserting an end portion of said tracheal tube through a tracheal tube opening in a gastric tube retainer of sheet material;

connecting an end portion of a ventilating circuit to said end portion of said tracheal tube so as to secure said gastric tube retainer between said end portions; and spreading apart portions of said gastric tube retainer along a slit and sliding a gastric tube along said slit into a gastric tube opening in said gastric tube retainer so that said gastric tube is anchored by said gastric tube retainer to said tracheal tube.

3. A method of retaining a gastric tube relative to a patient, comprising the steps of:

inserting a hub on one end of said tracheal tube through a tracheal tube opening in a gastric tube retainer of sheet material;

connecting an end portion of a ventilating circuit to said hub so as to secure said gastric tube retainer between said end portion of said ventilating circuit and a flange on said hub; and inserting a gastric tube into a gastric tube opening in said gastric tube retainer to anchor said gastric tube to said tracheal tube.

4. A method of retaining a gastric tube relative to a tracheal tube, which comprises the steps of:

securing a gastric tube retainer to said tracheal tube by engaging said gastric tube retainer between an end portion of said gastric tube and an end portion of a ventilating circuit; and engaging said gastric tube in said gastric tube retainer.

5. A method of retaining a gastric tube relative to a patient, comprising the steps of:

inserting a hub on one end of a tracheal tube through a tracheal tube opening in a gastric tube retainer of sheet material;

connecting an end portion of a ventilating circuit to said hub so as to secure said gastric tube retainer between said end portion of said ventilating circuit and a flange on said hub; and inserting a gastric tube into a gastric tube opening in said gastric tube retainer to anchor said gastric tube to said tracheal tube; and securing said tracheal tube to the patient by a tie around the patient's head.

* * * * *